United States Patent
Xing et al.

(10) Patent No.: US 11,675,029 B2
(45) Date of Patent: Jun. 13, 2023

(54) RETROSPECTIVE TUNING OF SOFT TISSUE CONTRAST IN MAGNETIC RESONANCE IMAGING

(71) Applicant: The Board of Trustees of the Leland Stanford Junior University, Stanford, CA (US)

(72) Inventors: Lei Xing, Palo Alto, CA (US); Yan Wu, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 3 days.

(21) Appl. No.: 17/632,457

(22) PCT Filed: Aug. 14, 2020

(86) PCT No.: PCT/US2020/046491
§ 371 (c)(1),
(2) Date: Feb. 2, 2022

(87) PCT Pub. No.: WO2021/034708
PCT Pub. Date: Feb. 25, 2021

(65) Prior Publication Data
US 2022/0276326 A1    Sep. 1, 2022

Related U.S. Application Data (60) Provisional application No. 62/888,363, filed on Aug. 16, 2019.

(51) Int. Cl.
*G01R 33/24* (2006.01)
*G01R 33/56* (2006.01)
*G06N 3/045* (2023.01)

(52) U.S. Cl.
CPC ....... *G01R 33/243* (2013.01); *G01R 33/5602* (2013.01); *G01R 33/5608* (2013.01); *G06N 3/045* (2023.01); *G01R 33/246* (2013.01)

(58) Field of Classification Search
CPC .............. G01R 33/243; G01R 33/5602; G01R 33/5608; G06N 3/045
See application file for complete search history.

(56) References Cited

U.S. PATENT DOCUMENTS

| | | | |
|---|---|---|---|
| 11,354,829 B2* | 6/2022 | Popescu | G06F 18/214 |
| 2018/0292484 A1* | 10/2018 | Hoppe | G06N 3/045 |

OTHER PUBLICATIONS

LeCun, Y., Bengio, Y. & Hinton, G. Deep learning. Nature 521, 436-444 (2015).

(Continued)

*Primary Examiner* — Gregory H Curran
(74) *Attorney, Agent, or Firm* — Lumen Patent Firm (57) ABSTRACT

Retrospective magnetic resonance imaging (MRI) uses a deep neural network framework [102] to generate from MRI imaging data [100] acquired by an MRI apparatus using a predetermined imaging protocol tissue relaxation parametric maps and magnetic/radiofrequency field maps [104] which are then used to generate using the Bloch equations [106] predicted MRI images [108] corresponding to imaging protocols distinct from the predetermined imaging protocol. This allows obtaining a wide spectrum of tissue contrasts distinct from those of the acquired MRI imaging data.

5 Claims, 8 Drawing Sheets

(56) References Cited

OTHER PUBLICATIONS

Wang, et al. Optimizing the precision in T1 relaxation estimation using limited flip angles. Magnetic Resonance in Medicine. Nov. 1987;5(5):399-416.

Messroghli, et al. Modified Look-Locker inversion recovery (MOLLI) for high-resolution T1 mapping of the heart. Magnetic Resonance in Medicine: An Official Journal of the International Society for Magnetic Resonance in Medicine 52.1 (2004): 141-146.

Deoni, et al. Rapid combined T1 and T2 mapping using gradient recalled acquisition in the steady state. Magnetic Resonance in Medicine 49.3 (2003): 515-526.

Warntjes, et al. Novel method for rapid, simultaneous T1, T* 2, and proton density quantification. Magnetic Resonance in Medicine: Magnetic Resonance in Medicine 57.3 (2007): 528-537.

Weiskopf, et al. "Quantitative multi-parameter mapping of R1, PD*, MT, and R2* at 3T: a multi-center validation." Frontiers in neuroscience 7 (2013): 95.

Ma, D., et al., Magnetic resonance fingerprinting. Nature, 2013. 495(7440): p. 187.

Tanenbaum, et al. Synthetic MRI for clinical neuroimaging: results of the Magnetic Resonance Image Compilation (MAGiC) prospective, multicenter, multireader trial. American Journal of Neuroradiology 38.6 (2017): 1103-1110.

Wang, et al. (2019). Echo planar time-resolved imaging (EPTI). Magnetic resonance in medicine, 81(6), 3599-3615.

Vaswani, et al. Attention is all you need. Advances in neural information processing systems. NIPS'17: Proceedings of the 31st International Conference on Neural Information Processing SystemsDecember 2017 pp. 6000-6010.

Kingma et al: A method for stochastic optimization, arXiv:1412.6980v9 [cs.LG], 2014.

Ma, et al., Whole knee joint T1 values measured in vivo at 3T by combined 3D ultrashort echo time cones actual flip angle and variable flip angle methods, Magnetic resonance in medicine, vol. 81, pp. 1634-1644, 2019.

Du, et al. Short T2 contrast with three-dimensional ultrashort echo time imaging. Magnetic resonance imaging 29.4 (2011): 470-482.

\* cited by examiner

RETROSPECTIVE TUNING OF SOFT TISSUE CONTRAST IN MAGNETIC RESONANCE IMAGING

CROSS-REFERENCE TO RELATED APPLICATIONS

This application is a 371 of PCT application PCT/US2020/046491 filed Aug. 14, 2020. PCT application PCT/US2020/046491 claims the benefit of U.S. Provisional application 62/888,363 filed Aug. 16, 2019.

FIELD OF THE INVENTION

The present invention relates generally to diagnostic imaging techniques. More specifically, it relates to methods for magnetic resonance imaging.

BACKGROUND OF THE INVENTION

Magnetic Resonance Imaging (MRI) provides soft tissue contrasts superior to other imaging modalities. The contrast between various tissues in an MR image arises principally from the difference in tissue properties ($T_1$, $T_2$, proton density p) as well as the imaging protocol. A flexible choice of the imaging protocol provides an opportunity to change the contrast between pathology and surrounding normal tissues, thus optimizing the visualization of individual pathology.

While versatility in tissue contrast is theoretically achievable and would be highly appreciated, tissue contrast obtained from standard clinical MRI is determined prior to data acquisition, which may not be the best to distinguish pathology of interest from surrounding normal tissues. Sometimes a repeated scan with a different imaging protocol is even needed.

SUMMARY OF THE INVENTION

The present invention provides techniques to enable retrospective tuning of soft tissue contrast in MRI. With these techniques, it is possible to adjust the contrast after image acquisition is completed. The techniques use a deep learning [1] based image processing methods with emulated pulse sequence or imaging parameter values to retrospectively change the soft tissue contrast in MRI.

According to one implementation, deep neural networks (e.g., self-attention convolutional neural networks) are trained to provide mappings from one or more conventional MR images already acquired in clinical practice to multiple tissue relaxation parametric maps ($T_1$, $T_2$, proton density p) and field maps ($B_0$, $B_1$). Thus, quantitative parametric maps are derived without additional data acquisition. Based on these predicted parametric maps and field maps, images that would have been acquired using other imaging protocols can be calculated with the application of the Bloch equations. This allows generation of images with a wide spectrum of tissue contrasts from a standard clinical exam. By deriving new images corresponding to alternative imaging parameter values or non-traditional pulse sequences, the techniques of the present invention can achieve three goals: (1) precisely adapt tissue contrast in an individual patient's MR images so as to provide optimal/personalized visualization of pathology, (2) normalize MR images acquired using inconsistent imaging protocols to enlarge data sets for quantitative analysis across or within medical centers, (3) obtain unconventional MR images without additional acquisition and therefore gain correlated clinical insights based on the new type of images.

In one aspect, the invention provides a method for retrospective magnetic resonance imaging (MRI) comprising obtaining MRI imaging data acquired by an MRI apparatus using a predetermined imaging protocol; computing from the imaging data by a deep neural network tissue relaxation parametric maps and magnetic/radiofrequency field maps; and generating from the tissue relaxation parametric maps and magnetic/radiofrequency field maps using Bloch equations predicted MRI images corresponding to imaging protocols distinct from the predetermined imaging protocol.

In one implementation, the deep neural network comprises an encoder contracting path and a decoder expanding path with global and local shortcut connections embedded; and convolutional blocks, each having a self-attention layer in additional to a convolutional layer and an activation layer.

Preferably, the MRI imaging data has a predetermined tissue contrast corresponding to the predetermined imaging protocol, wherein the predetermined imaging protocol comprises imaging parameter values and pulse sequences, and wherein the predicted MRI image has a tissue contrast distinct from the predetermined tissue contrast.

In one implementation, the MRI imaging data comprises qualitative MRI images including (but not limited to) a $T_1$ weighted image and a $T_2$ weighted image.

In one implementation, the tissue relaxation parametric maps comprise $T_1$, $T_2$, and $\rho$ maps, and wherein the magnetic/radiofrequency field maps comprise $B_0$ and $B_1$ maps.

Applications of these techniques include the following:
The method can be used to optimize the visualization of individual pathology by retrospectively changing imaging parameter value and corresponding tissue contrast in MR images of an individual patient.
The techniques of the present invention can be used to derive new images presumably acquired using non-traditional pulse sequences that are not included in a standard clinical MRI exam.
The present invention has potential utility in radiomics since it can help to normalize MR images acquired using inconsistent imaging protocols.

DETAILED DESCRIPTION

The inventors have discovered that quantitative parametric maps can be derived from one or more MR images acquired in a standard clinical MRI exam without extra data acquisition; subsequently, these quantitative parametric maps can be used to synthesize various MRI images corresponding to different imaging protocols with the application of the Bloch equations.

Retrospective tuning of tissue contrast in MRI is technically feasible if tissue relaxation parametric maps (of $T_1$, $T_2$, p) are known. Given tissue parametric maps, MR images with alternative contrasts (assuming other imaging protocols are adopted) can be obtained with the application of the Bloch equations. However, tissue relaxation parametric maps are typically hard to obtain in clinical practice, which is mainly due to extra data acquisition required by parameter quantification and correction for system imperfection (e.g., magnetic/radiofrequency field inhomogeneity, and interscan motion).

Using deep learning, multiple tissue relaxation parametric maps may be derived from one or more MR images acquired in a standard clinical MRI exam. This approach is fundamentally different from the existing ones in that all the information needed for multi-parametric mapping is extracted without additional data acquisition involved. In particular, the compensation for magnetic/radiofrequency field inhomogeneity is automatically achieved without specific measurement.

Leveraging from this deep learning-based multi-parametric mapping, the present technique provides a novel paradigm that provides a spectrum of soft tissue contrasts from a standard clinical MRI exam. Deep neural networks are trained to derive multiple tissue relaxation parametric maps from one or more MR images already acquired. Subsequently, from the estimated parametric maps, MR images with different contrasts can be calculated using the Bloch equations.

Figure 1A:
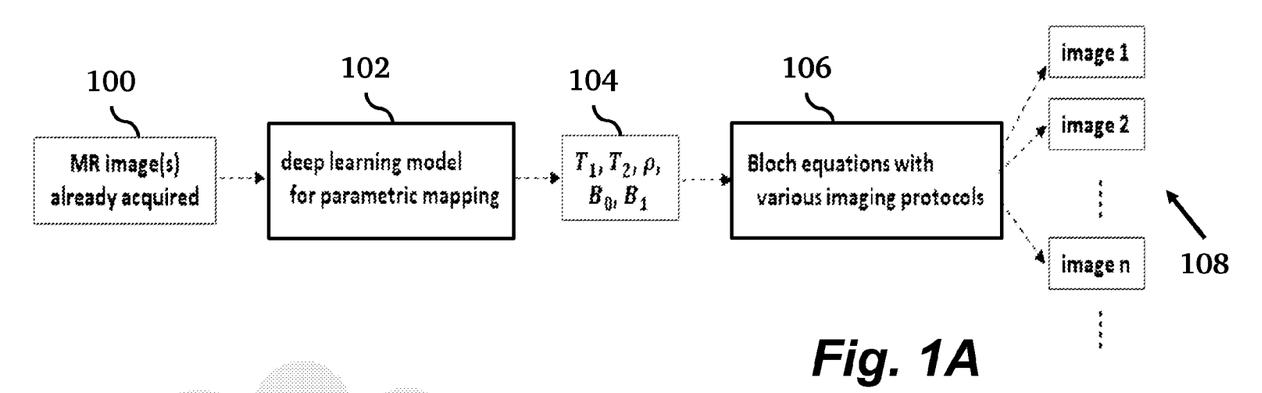
FIG. 1A is a processing pipeline of retrospective tuning of tissue contrast in MRI according to an embodiment of the invention.
Figure 1B:
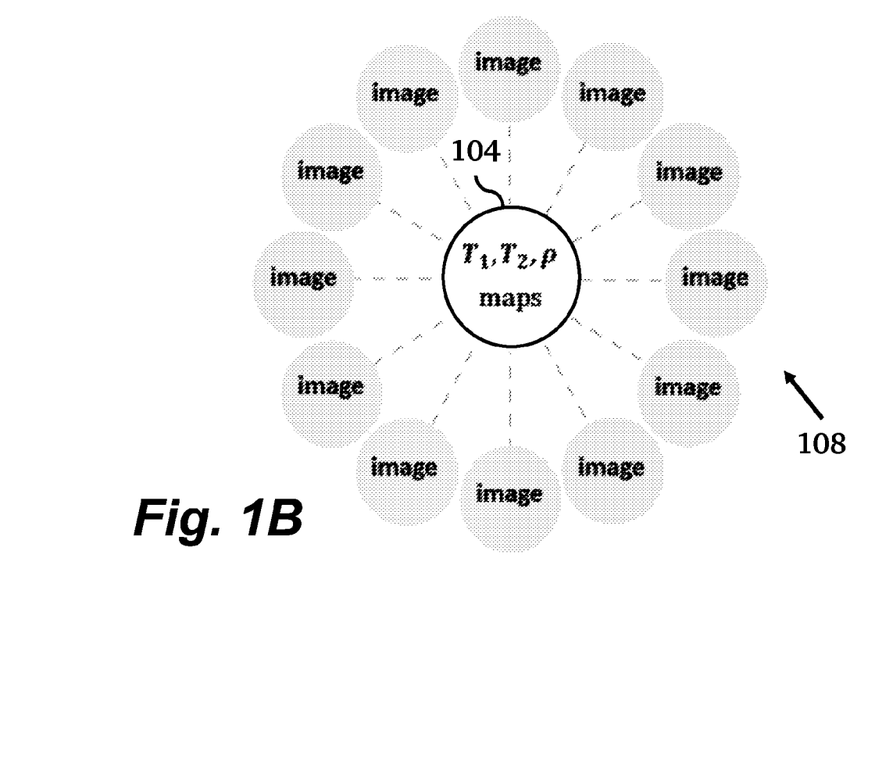
FIG. 1B is a schematic diagram illustrating how all the MR images of an individual subject stem from the same tissue relaxation parametric maps and can be consequently mapped to one another, according to an embodiment of the invention.

FIGS. 1A, 1B illustrate a generic framework that permits diversity in both input and output images. On the one hand, no specific weighting ($T_1$, $T_2$, or others) is required on input images; on the other hand, MR images presumably acquired using a variety of pulse sequences or imaging parameter values can be derived as the output. Using the present approach, without any additional image acquisition, a wide spectrum of tissue contrasts can be obtained.

FIG. 1A shows a processing pipeline of retrospective tuning of tissue contrast in MRI. One or more MR images already acquired 100 are input to a deep learning model for parametric mapping 102, which generates as output tissue relaxation parametric maps and field maps 104. Using the Bloch equations with one or more imaging protocols 106, new images 108 are produced which presumably would have been acquired using other imaging protocols. This technique thus is capable of generating images with a wide spectrum of tissue contrasts without extra data acquisition.

In step 102, one or more images 100 already acquired in standard clinical MRI are used to predict tissue relaxation parametric maps ($T_1$, $T_2$, p) and field maps ($B_0$, $B_1$) 104 with the help of deep neural networks. Notice that no specific weighting is required for the input images 100. In step 106, given the predicted parametric maps and field maps 104, image acquisition protocols are chosen to derive new images 108 with the application of the Bloch equations. The underlying reason that supports the transformation of signal intensity in MR image is that all the MR images of an individual subject are derived from the same tissue relaxation parametric maps and can be consequently mapped to one another with the relationship defined by the imaging protocols. This relationship between various images 108 and the parametric maps and field maps 104 is schematically illustrated in FIG. 1B.

Deep Learning Based Quantitative Parametric Mapping and Variable Contrast Image Prediction According to the techniques of the present invention, deep neural networks are trained to produce tissue relaxation parametric maps from one or more MR images already acquired in clinical practice. In the training, one or more MR images that were acquired using a specific imaging protocol are fed into deep neural networks as the input images, and the corresponding tissue relaxation parametric maps are used as the ground truth, which were measured using conventional approaches (e.g., variable flip angle [2], MOLLI [3], $DESPOT_1$ and $DESPOT_2$[4], MR multitasking [5, 6], MR fingerprinting [7], MAGiC [8], EPTI [9]).

Figure 2A:
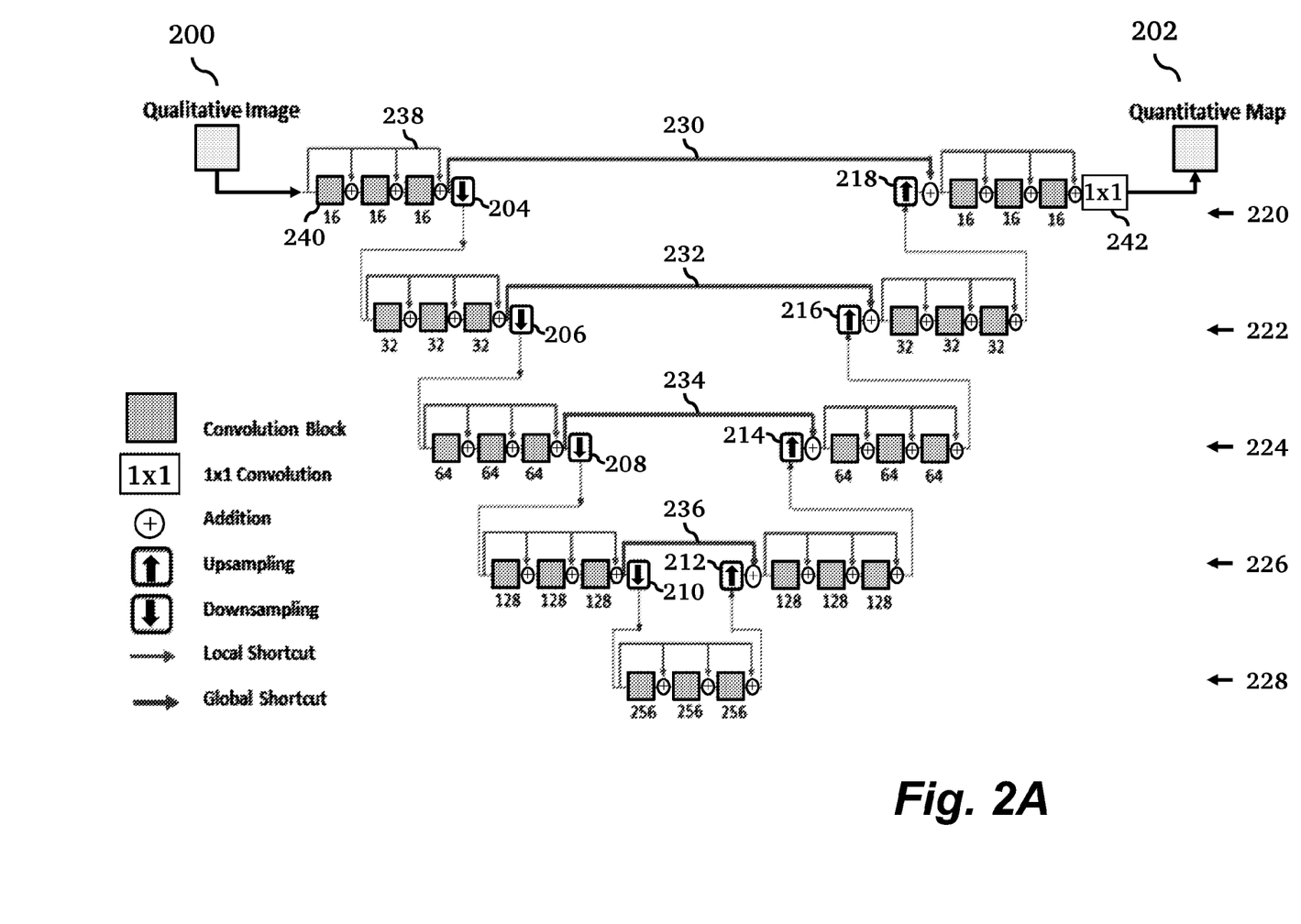
FIG. 2A is a diagram illustrating the architecture of a self-attention convolutional neural network used for quantitative parametric mapping according to an embodiment of the invention.

FIG. 2A shows an example of a convolutional neural network (CNN) framework constructed to implement the deep neural network according to one embodiment of the invention. This self-attention convolutional neural network for quantitative parametric mapping prediction has a hierarchical architecture of the deep convolutional neural network composed of an encoder and a decoder with global and local shortcut connections. A qualitative image 200 is input on the left and a corresponding quantitative map 202 is output on the right. The deep convolutional neural network has a hierarchical architecture composed of a contracting path with four down-samplings 204, 206, 208, 210, followed by a subsequent expanding path with four up-samplings 212, 214, 216, 218. Along the contracting path, the resolution of feature maps halves via down-sampling, and the number of feature maps or convolutional kernels doubles. Along the expanding path, the resolution of feature maps doubles via up-sampling, and the number of feature maps halves. In this example, there are five levels 220, 222, 224, 226, 228, where the number of feature maps in each level is respectively 16, 32, 64, 128, 256. Each level is composed of three sequential convolution blocks (e.g., convolution block 240). Global shortcut connections 230, 232, 234, 236 are established between the corresponding levels of the contracting and expanding paths to compensate for details lost in down-sampling, whereas local shortcut connections (e.g., 238) across convolution blocks within the same level of a single path are established to facilitate residual learning. The output of the last level of the expanding path is convolved with a 1×1 kernel 242, producing an output quantitative map 202.

Figure 2B:
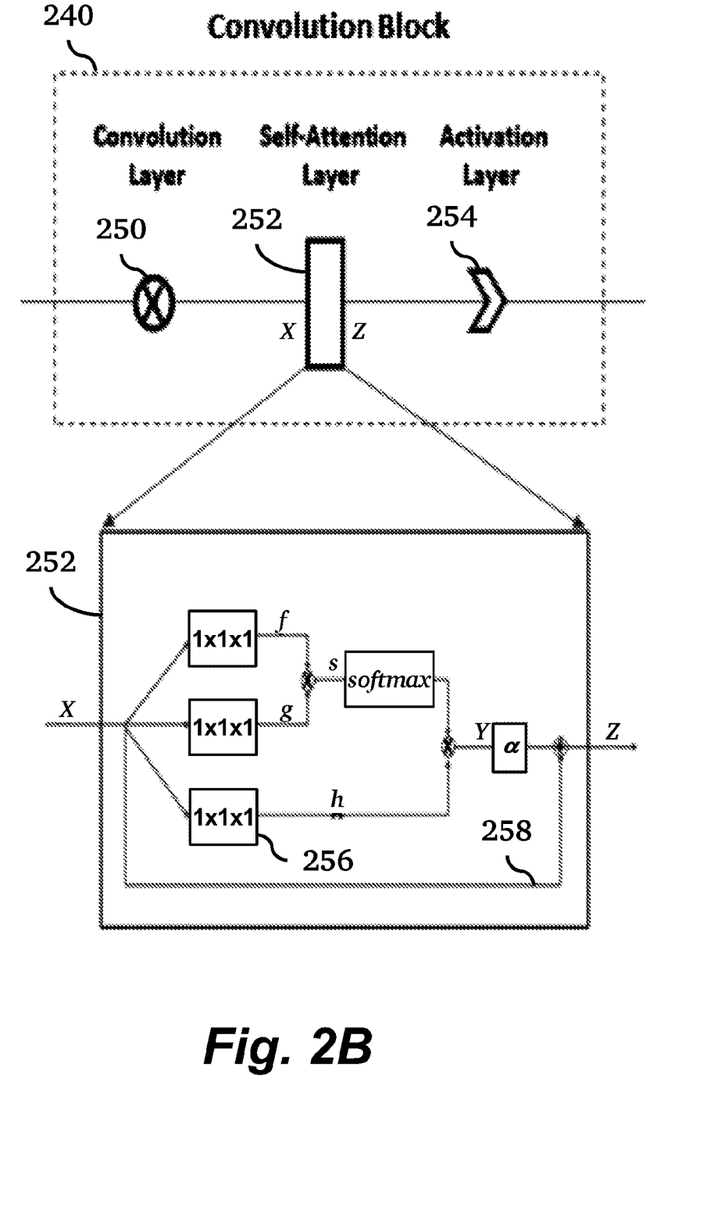
FIG. 2B shows the structure of a convolutional block used in the architecture of FIG. 2A, according to an embodiment of the invention.

FIG. 2B shows the detail of a convolutional block 240 used in the levels of the network shown in FIG. 2A. The block is composed of a convolution layer 250 followed by a self-attention layer 252 and an activation layer 254. The self-attention layer 252 is integrated to make efficient use of non-local information. The attention value is determined by the relevance (s) between the current position and another position as well as the feature value (h) at another position.

Attention mechanism [10] is incorporated in preferred embodiments of the invention to make efficient use of non-local information. Briefly, the convolution operator has a local receptive field, which can be problematic for getting non-local a priori knowledge (e.g., the location of a voxel in an anatomy). The receptive field can be enlarged by increasing the depth of the network, which however introduces difficulties in optimization when long-range dependencies are progressively propagated across multiple layers. A self-attention CNN is used to overcome this limitation. Direct interactions are established between all voxels within a given image, where more attention is focused on regions that contain similar spatial information. In every convolutional block, a self-attention map is derived by attending to all the positions in the feature map obtained in the previous convolutional layer. The value at a position of the attention map is determined by two factors. One is the relevance between the signals at current position i and other position j, defined by an embedded Gaussian function $s(X_i, X_j)=\exp\{(W_f X_i)'(W_g X_j)\}$. The other is a representation of the feature value at the other position j, given by a linear function $h(X_j)=W_h X_j$. Here, $W_f$, $W_g$, and $W_h$ are weight matrices (implemented as 1×1×1 convolution 256), whose optimal values are identified by the model in training. Within each attention layer, a shortcut connection 258 is established to include local features as well. The contributions of local and non-local information are balanced by a scale parameter a, whose value is also determined in training.

The deep neural network is trained for quantitative parametric mappings. The loss function used in training is defined as a combination of SSIM (structural similarity index) and $l_1$ norm, where $l_1$ norm is mainly responsible for minimizing uniform biases, and SSIM preserves local structure and contrast in high-frequency regions. In one implementation, an empirical loss function we adopt is loss=$l_1$+5*SSIM. With errors backpropagated, model parameters are updated using the Adam algorithm [11] with $\alpha=0.001$, $\beta_1=0.89$, $\beta_2=0.89$, and $\epsilon=10^{-8}$.

Notice that a different kind of deep neural network (e.g., other convolutional neural network or generative adversarial network) can be used for parametric mapping with slightly different performance. Moreover, instead of using an individual deep neural network for the derivation of a particular type of parametric maps (e.g., one network for $T_1$ mapping, and another for $T_2$ mapping), a single deep neural network that produces multiple outputs may be used for simultaneous derivation of multiple quantitative parametric maps (e.g., a starGAN for the prediction of $T_1$, $T_2$, $\rho$, $B_0$, and $B_1$ maps).

Given estimated tissue parametric maps, MR image that would have been presumably acquired using other imaging protocol can be calculated. For example, to generate $T_1$-weighted SPGR image, the signal intensity is calculated as $$S = \rho \cdot \sin(\alpha) \frac{1-e^{-TR/T_1}}{1-\cos(\alpha) \cdot e^{-TR/T_1}},$$

and tissue contrast can be changed by tuning the value of imaging parameter (e.g., flip angle α, TR). Here, $B_1$ inhomogeneity is taken into consideration via $\alpha=\alpha_{nominal} \cdot B_1$, where $\alpha_{nominal}$ is the nominal flip angle specified by the imaging protocol, and α is the actual flip angle that takes effects. For $T_2$-weighted FSE images, the signal intensity is given by $S=\rho \cdot e^{-TE/T_2}$, and tissue contrast can be changed by tuning the value of imaging parameter (e.g., TE). In a similar way, images with other types of weighting can be generated. In addition to the signal intensity equations, the extended phase graph theory can be employed to calculate the signal intensity as well. We emphasize that a wide spectrum of contrasts can be achieved beyond the contrasts specified in training data.

Accuracy of MR Parametric Mapping

In a preliminary study, for each subject, $T_1$-weighted images are acquired using a 3D UTE (ultra-short echo time) sequence with variable flip angles (5°, 10°, 20°, and 30°); and $T_2$-weighted images are acquired using the UTE sequence with variable TEs (at 0.032, 4.4, 8.8, 13.2, 17.6 and 22 ms). Quantitative $T_1$ map and $T_2$ map are extracted using conventional least square fitting approach.

Figure 3A:
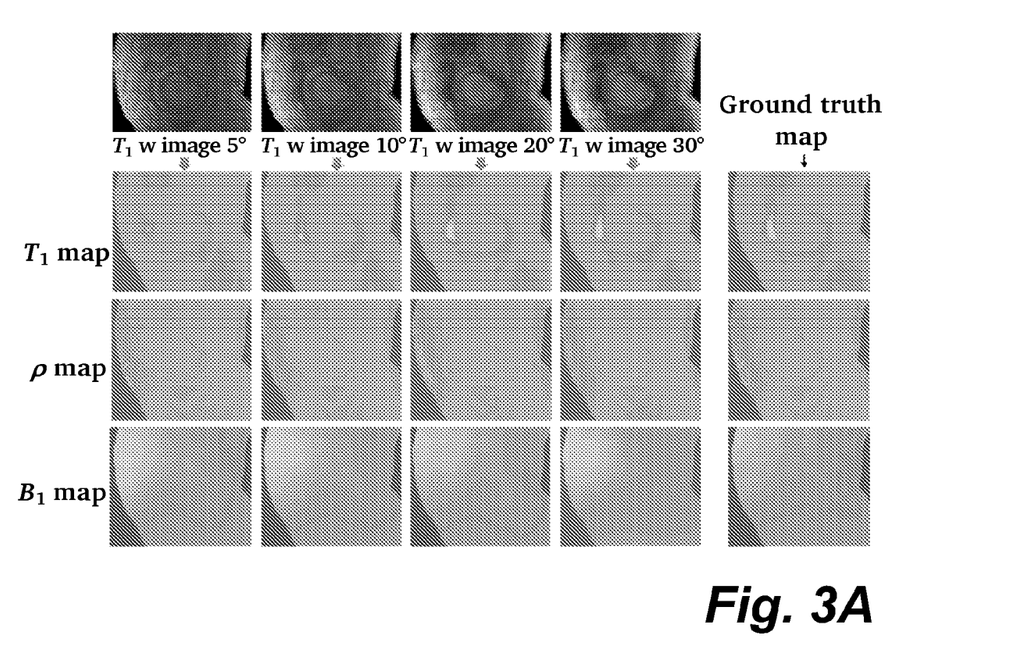
FIG. 3A is an image grid illustrating the prediction of $T_1$, $\rho$ and $B_1$ maps from a single $T_1$-weighted image, according to an embodiment of the invention.
Figure 3B:
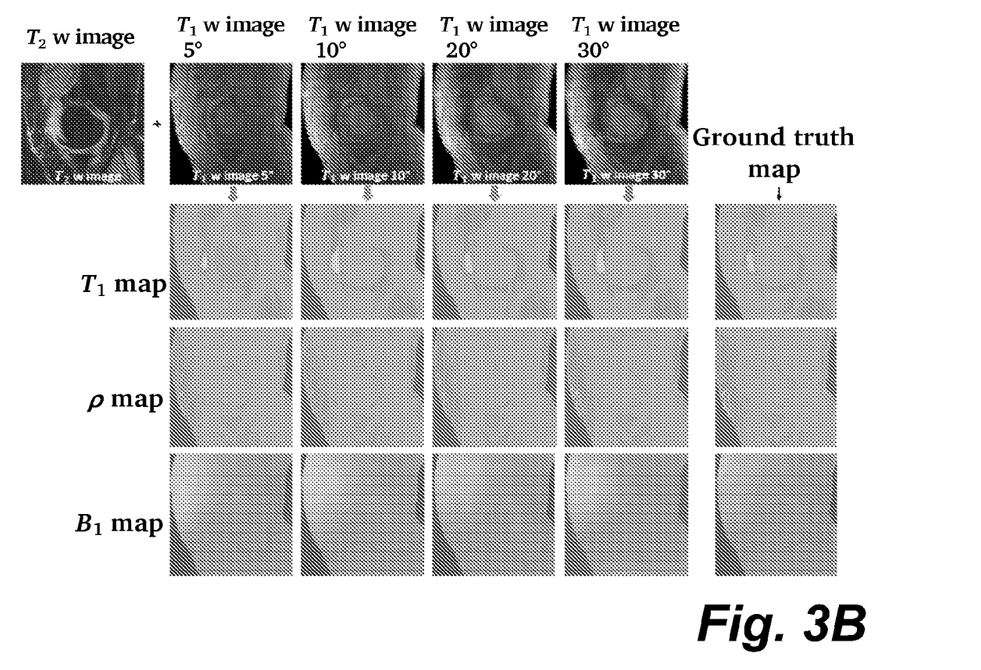
FIG. 3B is an image grid illustrating the prediction of $T_1$, $\rho$ and $B_1$ maps from a combination of $T_1$- and $T_2$-weighted images, according to an embodiment of the invention.

Deep learning models were trained for quantitative parametric mapping. As shown in FIGS. 3A, 3B, quantitative $T_1$, ρ, and $B_1$ maps of every subject are predicted from a $T_1$-weighted image with or without a $T_2$-weighted image. FIG. 3A shows prediction of $T_1$, ρ and $B_1$ maps from a single $T_1$-weighted image, while FIG. 3B shows prediction of $T_1$, ρ and $B_1$ maps from a combination of $T_1$- and $T_2$-weighted images. In each case, the input $T_1$-weighted image is acquired with a flip angle of 5°, 10° 20°, or 30°, and the input $T_2$-weighted image is acquired with TEs of 4.4 ms. High fidelity has been achieved between the ground truth maps (shown in the rightmost column) and the predicted maps obtained from different input images. Even from a single $T_1$-weighted image, high fidelity has been achieved in the predicted $T_1$, ρ, and $B_1$ maps. When an additional $T_2$-weighted image is incorporated, the prediction accuracy is slightly increased.

Figure 4:
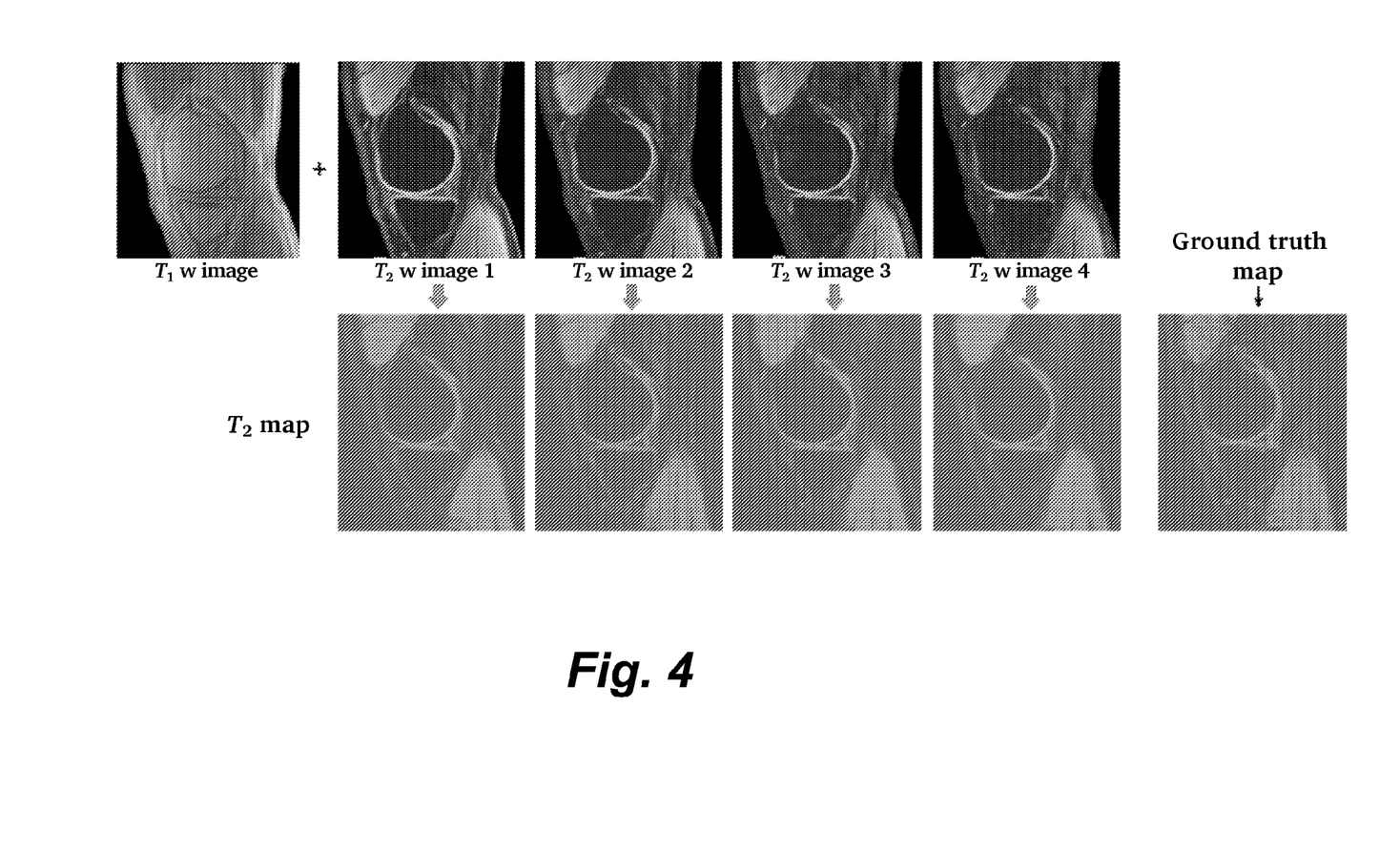
FIG. 4 is an image grid illustrating and example of the prediction of $T_2$ map from a combination of $T_1$- and $T_2$-weighted images, according to an embodiment of the invention.

Similarly, we trained deep neural networks to derive quantitative $T_2$ map of every subject from a $T_1$-weighted image and a $T_2$-weighted image, as shown in FIG. 4. High fidelity has been achieved as well. FIG. 4 shows prediction of $T_2$ map from a combination of $T_1$- and $T_2$-weighted images. In every column, the input $T_2$-weighted image is acquired with a different TE of (4.4, 8.8, 13.2, or 17.6 ms) with a $T_1$-weighted image obtained using a flip angle of 20°. High fidelity has been achieved between the ground truth maps and all the predicted maps.

The results have been quantitatively evaluated. For $T_1$, $T_2$, ρ and $B_1$ mapping, the on correlation coefficients range from 0.95 to 0.99; the $l_1$ errors are from 0 0.01 to 0.10. The results are relatively stable when different input images are adopted. The accurate parametric mapping lays a solid foundation for variable contrast image prediction.

Accuracy of Variable Contrast Image Prediction

Figure 5:
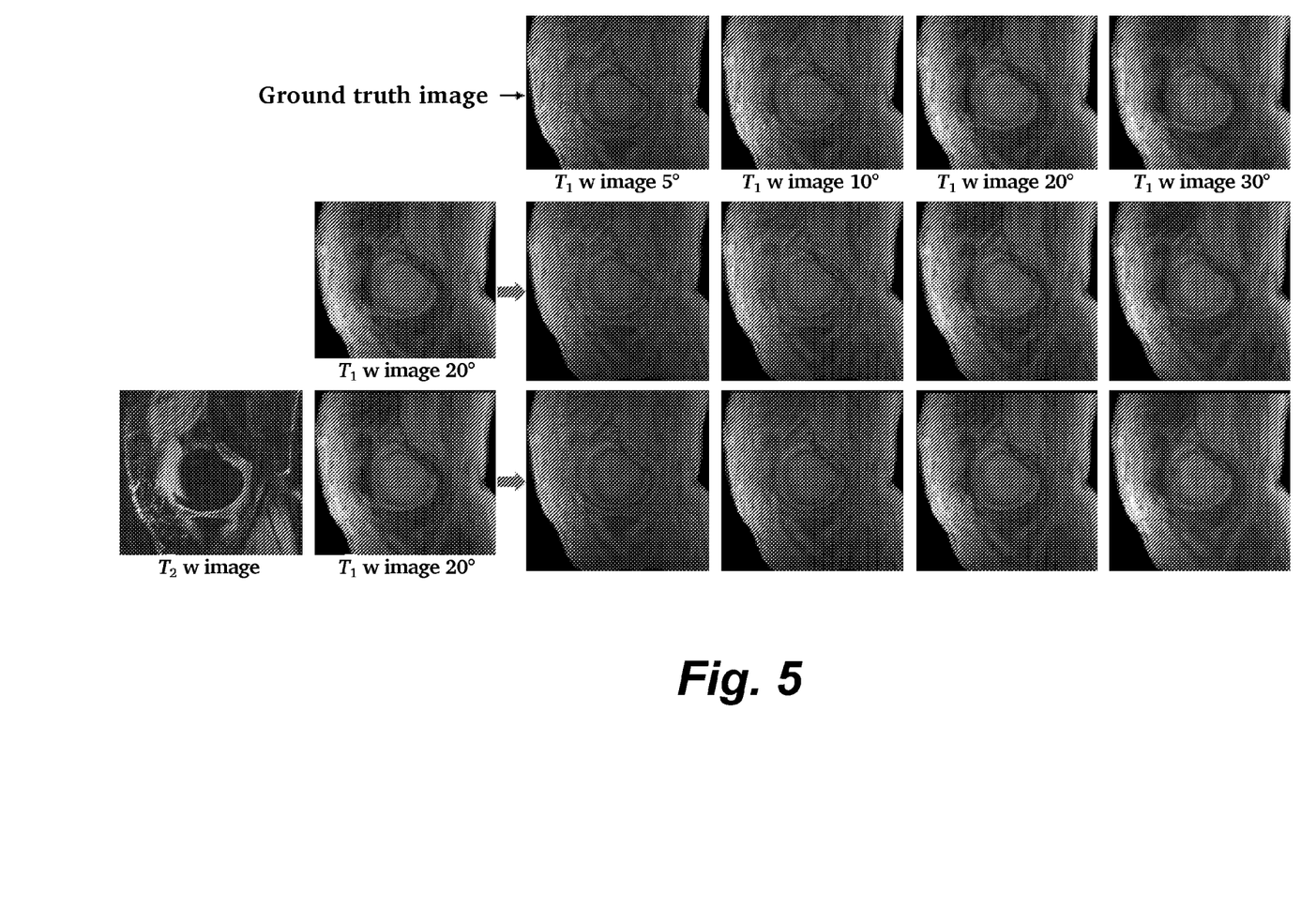
FIG. 5 is an image grid illustrating and example how $T_1$-weighted images corresponding to various flip angles are obtained from a $T_1$-weighted image acquired using a single flip angle, with or without a $T_2$-weighted image, according to an embodiment of the invention.

Given predicted tissue relaxation parametric maps, various images can be generated with the application of the Bloch equations, assuming other imaging parameter values or pulse sequences are adopted. An example is demonstrated in FIG. 5. In the techniques of the present invention, $T_1$-weighted images corresponding to the given flip angles (5°, 10° 20°, and 30°) are obtained from a $T_1$-weighted image (acquired using a flip angle of 20°. The first row shows the ground truth, the second row shows images generated without a $T_2$-weighted image, the third row shows images generated with a $T_2$-weighted image (acquired using a TE of 4.4 ms). High fidelity has been achieved between the predicted images and the ground truth.

The overall results have been quantitatively evaluated. The correlation coefficients range from 0.94 to 0.99, and the $l_1$ errors are between 0.04 and 0.13, depending on the pulse sequence and imaging parameter value used. The results are relatively stable when different input images are adopted.

Discussion

A new paradigm is presented for retrospective tuning of contrast between different tissues in an MR image. This is different from window leveling, where signal intensity is changed based on histogram (not based on tissue type).

Retrospective tuning of tissue contrast in MRI can be used to optimize the visualization of pathology. The best way to distinguish pathology from the surrounding normal tissues does vary with characteristics of pathologies and surrounding normal tissues. Using the techniques of the present invention, unlimited possibilities of tissue contrasts are offered, which include optimal visualization of individual pathology. Alternatively, a direct mapping can be established between input and output images that have different contrasts. In prior approached, attainable tissue contrasts are limited to those provided in the training data, which might not be optimal for the visualization of individual patient pathology.

In the present approach, deep learning plays a key role by exploiting the relationship between MR image and quantitative maps. This implicit relationship facilitates the transformation of signal intensity in MR image, since images of the same subject with different tissue contrasts all derive from the same tissue relaxation parametric maps. Deep learning has unprecedented ability to learn complex relationships and to incorporate existing knowledge into the inference model through feature extraction and representation learning. In the quantitative parametric mapping used in the present invention, deep learning demonstrates strong capability to separate out different contributing factors whose influences are intertwined in an MR image (e.g., tissue relaxation parameters and $B_1$).

Based on the deep learning-based parametric mapping approach, versatile tissue contrasts can be obtained without additional data acquisition. Tissue contrast in MRI can be retrospectively tuned and adapted to optimize the visualization of individual pathology. The proposed approach has the potential to emulate images presumably acquired using non-traditional pulse sequences, from which new insights on the characteristics of pathologies may be gained.

Image Acquisition

In general, conventional qualitative MR images are acquired using a consistent imaging protocol, which will be used as input images to deep neural network models for tissue parametric mapping (e.g., $T_1$ weighted images acquired using the spoiled gradient echo sequence, $T_2$ weighted images obtained using the fast spin echo sequence). Meanwhile, $T_1$ and $T_2$ maps are derived using conventional quantitative parametric mapping methods (e.g., variable flip angle, MOLLI, DESPOT$_1$ and DESPOT$_2$) or multi-parametric mapping approach (e.g., MR fingerprinting, MR multitasking, MAGiC, EPTI), which will be used as the ground truth of the prediction models. $B_1$ map may be acquired using conventional methods (e.g., actual flip angle method).

In this study, the training and testing images are acquired from 56 subjects [12, 13]. For each subject, four $T_1$-weighted images are acquired, where a 3D ultra-short echo time (UTE) sequence is used with variable flip angles (5°, 10°, 20°, and 30° with a very short echo time (TE) of 32 µs and a time of repetition (TR) of 20 ms. $B_1$ map of each subject is measured using an actual flip angle imaging sequence with a TE of 32 µs, two interleaved TRs (20/100 ms) and a flip angle of 45°, and $T_1$ map is extracted from $T_1$-weighted images via conventional least square fitting and corrected by $B_1$ map. Furthermore, for each subject, six $T_2$-weighted images are acquired using a 3D UTE sequence with TEs of 0.032, 4.4, 8.8, 13.2, 17.6 and 22 ms, a TR of 500 ms, and a flip angle of 20°. $T_2$ map is derived using conventional least square fitting.

Examples of Variable Contrast Images Produced by the Techniques of the Present Invention The techniques of the present invention provide a generic framework for retrospective tuning of tissue contrast in MRI. Images that would have been presumably acquired using different imaging parameters or pulse sequences can be generated to provide versatile tissue contrasts.

Figure 6:
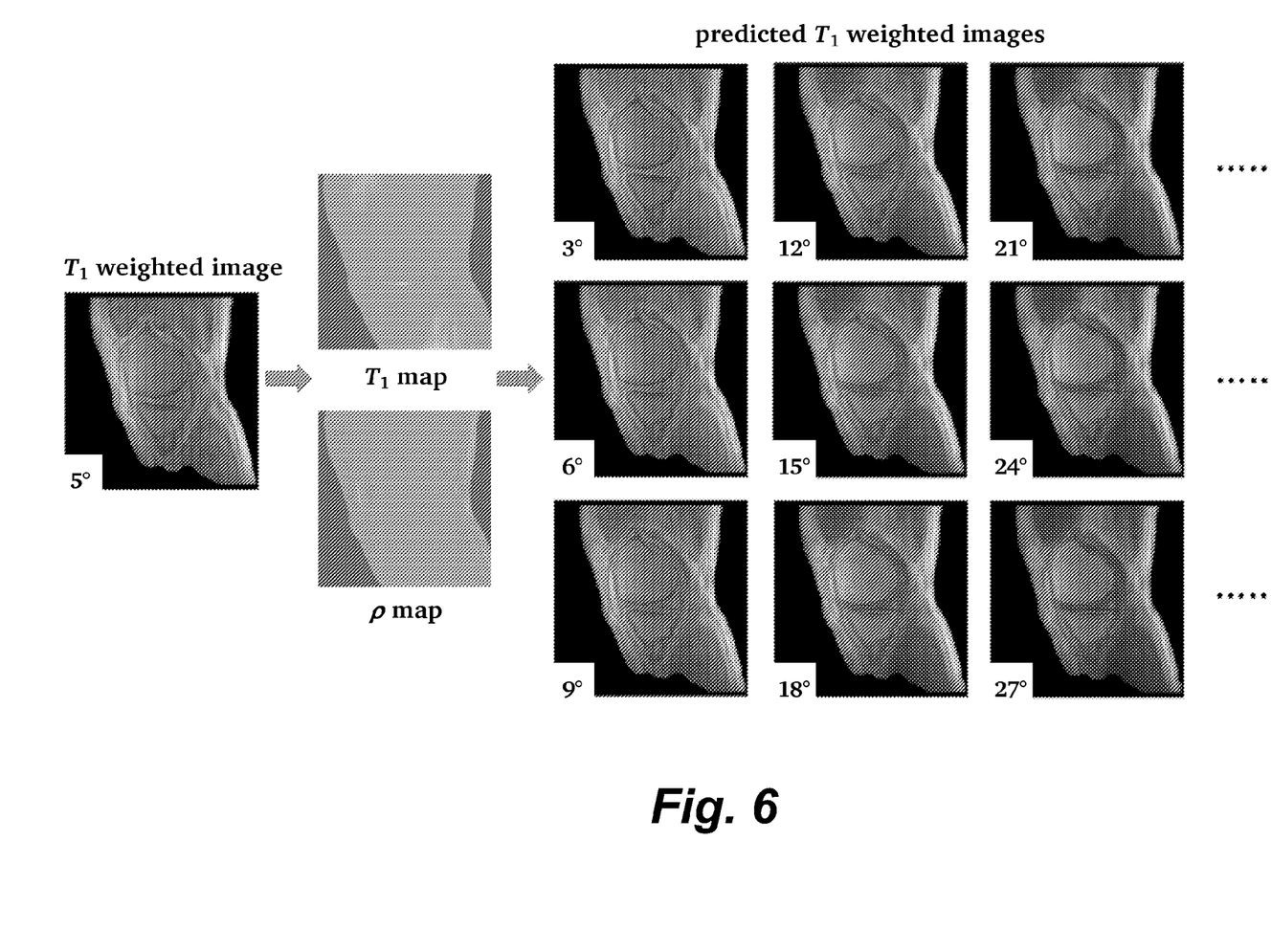
FIG. 6 is an image grid illustrating an example of how variable flip angle $T_1$-weighted images are derived from a single $T_1$-weighted input image, according to an embodiment of the invention.

FIG. 6 shows an example using the techniques of the present invention, where variable flip angle $T_1$-weighted images are derived from a single $T_1$-weighted input image. From a $T_1$-weighted input image acquired using a flip angle of 5°, $T_1$ map and ρ map are predicted, which are subsequently used to calculate other $T_1$-weighted images with the application of the Bloch equations. Diverse $T_1$ weightings are achieved by changing the flip angle in the UTE sequence at a much finer scale (every 3° than the one adopted in the actual measurements (only 4 angles are employed in all)

Figure 7:
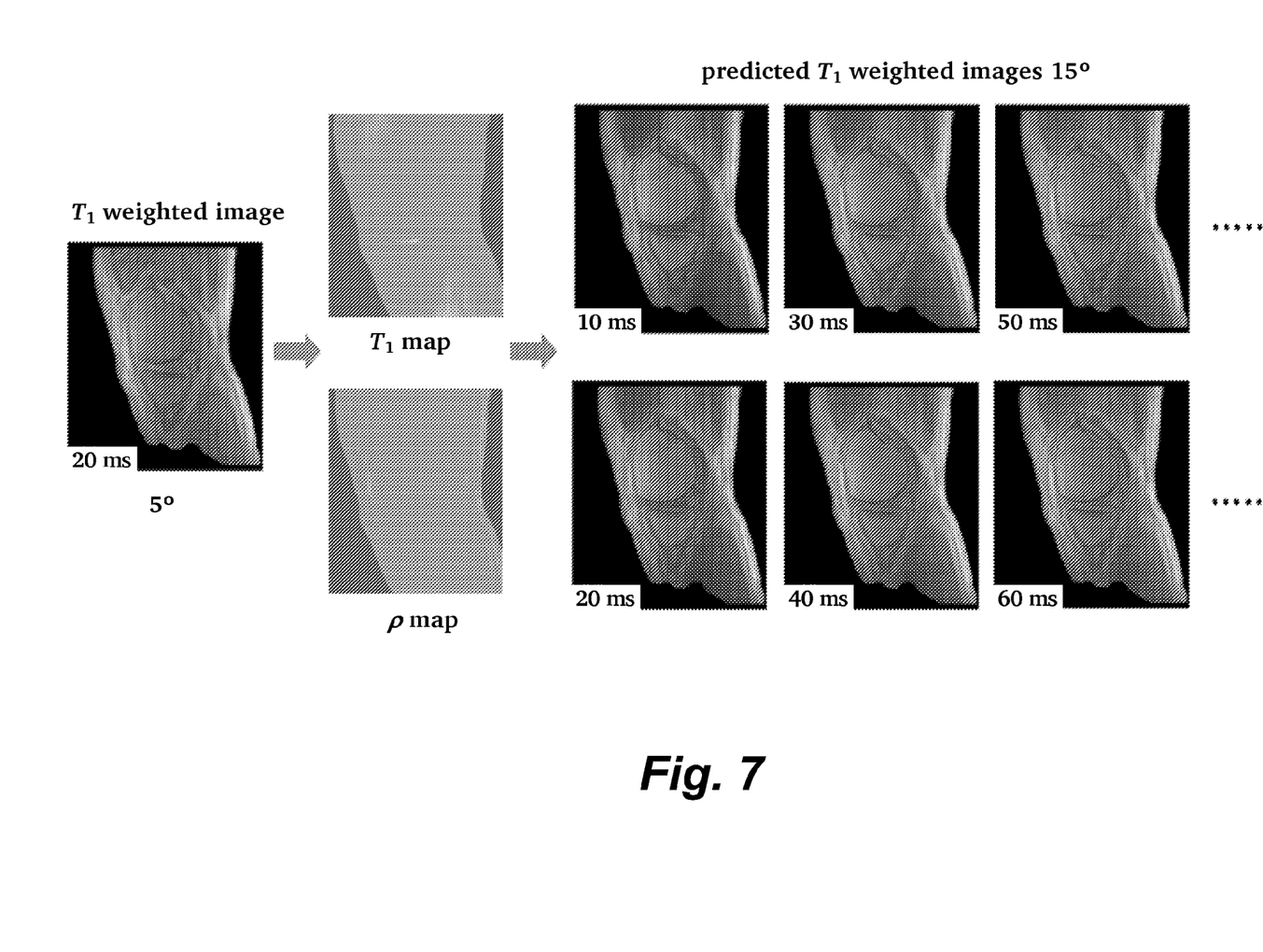
FIG. 7 is an image grid illustrating an example of how more contrast images are obtained from a single $T_1$-weighted input image, according to an embodiment of the present invention.

Similarly, TR in the same sequence can be varied to offer versatile contrasts, as shown in FIG. 7. Using the techniques of the present invention, more contrasts are obtained from a single $T_1$-weighted input image, presumable using variable TRs and flip angles. From a $T_1$-weighted input image acquired using a TR of 20 ms and a flip angle of 5°, $T_1$ map and ρ map are predicted, which are subsequently used to calculate alternative $T_1$-weighted images presumably acquired using another flip angle)(15°) and variable TRs.

In addition to the techniques described in preferred embodiments, the inventors also envision the following variations within the scope of the invention:

Instead of using the self-attention convolutional neural network as described above, a different kind of deep neural network (e.g., other convolutional neural network or generative adversarial network) may be used for the quantification of a specific type of parametric maps (e.g., $T_1$, $T_2$, ρ, $B_0$, or $B_1$ map).

Instead of using an individual deep neural network for the derivation of a particular type of parametric maps (e.g., one network for $T_1$ mapping, and another for $T_2$ mapping), a single deep neural network that produces multiple outputs may be used for simultaneous derivation of multiple quantitative parametric maps (e.g., a starGAN for the prediction of $T_1$, $T_2$, ρ, $B_0$, and $B_1$ maps).

Deep learning models may be trained to derive quantitative parametric maps from different types of input images, which were acquired using alternative pulse sequences (e.g., spoiled gradient echo, steady state free precession) or imaging parameter values (e.g., TR, TE, flip angle).

Ground truth parametric maps may be derived using various quantitative MRI approaches (e.g., variable flip angle, MOLLI, DESPOT$_1$ and DESPOT$_2$, MR fingerprinting, MR multitasking, MAGiC, EPTI).

Given quantitative parametric maps as well as an emulated pulse sequence and imaging parameter values, the signal intensity of the new image may be calculated using extended phase graph theory instead of signal intensity equations.

The proposed retrospective contrast tuning method can be implemented on any MRI system as long as training data and testing data are acquired in the same type of scanners.

The deep learning models can be trained in any computer system, preferably with GPU cards.

REFERENCES

1. Y. LeCun, Y. Bengio, and G. Hinton, "Deep learning," *nature*, vol. 521, p. 436, 2015.
2. Wang, Henry Z., Stephen J. Riederer, and James N. Lee. "Optimizing the precision in T1 relaxation estimation using limited flip angles." *Magnetic Resonance in Medicine* 5.5 (1987): 399-416.
3. Messroghli, Daniel R., et al. "Modified Look-Locker inversion recovery (MOLLI) for high-resolution T1 mapping of the heart." *Magnetic Resonance in Medicine: An Official Journal of the International Society for Magnetic Resonance in Medicine* 52.1 (2004): 141-146.
4. Deoni, Sean C L, Brian K. Rutt, and Terry M. Peters. "Rapid combined T1 and T2 mapping using gradient recalled acquisition in the steady state." *Magnetic Resonance in Medicine* 49.3 (2003): 515-526.
5. Warntjes, J. B. M., O. Dahlqvist, and Peter Lundberg. "Novel method for rapid, simultaneous T1, T* 2, and proton density quantification." *Magnetic Resonance in Medicine: Magnetic Resonance in Medicine* 57.3 (2007): 528-537.
6. Weiskopf, Nikolaus, et al. "Quantitative multi-parameter mapping of R1, PD*, MT, and R2* at 3T: a multi-center validation." *Frontiers in neuroscience* 7 (2013): 95.
7. Ma, D., et al., Magnetic resonance fingerprinting. Nature, 2013. 495(7440): p. 187.
8. Tanenbaum, Lawrence N., et al. "Synthetic MRI for clinical neuroimaging: results of the Magnetic Resonance Image Compilation (MAGiC) prospective, multicenter, multireader trial." *American Journal of Neuroradiology* 38.6 (2017): 1103-1110
9. Wang, F., Dong, Z., Reese, T. G., Bilgic, B., Katherine Manhard, M., Chen, J., . . . & Setsompop, K. (2019). Echo planar time-resolved imaging (EPTI). Magnetic resonance in medicine, 81(6), 3599-3615.
10. Vaswani, Ashish, et al. "Attention is all you need." *Advances in neural information processing systems.* 2017.
11. D. P. Kingma and J. Ba, "Adam: A method for stochastic optimization," *arXiv preprint arXiv:* 1412.6980, 2014
12. Y. J. Ma, W. Zhao, L. Wan, T. Guo, A. Searleman, H. Jang, et al., "Whole knee joint T1 values measured in vivo at 3T by combined 3D ultrashort echo time cones actual flip angle and variable flip angle methods," *Magnetic resonance in medicine, vol.* 81, pp. 1634-1644, 2019.
13. Du, Jiang, et al. "Short T2 contrast with three-dimensional ultrashort echo time imaging." Magnetic resonance imaging 29.4 (2011): 470-482.

The invention claimed is:

1. A method for retrospective magnetic resonance imaging (MRI) comprising:
   obtaining MRI imaging data acquired by an MRI apparatus using a predetermined imaging protocol;
   computing from the imaging data by a deep neural network tissue relaxation parametric maps and magnetic/radiofrequency field maps;
   generating from the tissue relaxation parametric maps and magnetic/radiofrequency field maps using Bloch equations predicted MRI images corresponding to imaging protocols distinct from the predetermined imaging protocol.

2. The method of claim 1 wherein the deep neural network comprises
   an encoder contracting path and a decoder expanding path with global and local shortcut connections embedded;
   convolutional blocks, each having a self-attention layer in additional to a convolutional layer and an activation layer.

3. The method of claim 1 wherein the MRI imaging data has a predetermined tissue contrast corresponding to the predetermined imaging protocol, wherein the predetermined imaging protocol comprises imaging parameter values and pulse sequences, and wherein the predicted MRI image has a tissue contrast distinct from the predetermined tissue contrast.

4. The method of claim 1 wherein the MRI imaging data comprises qualitative MRI images including a $T_1$ weighted image and a $T_2$ weighted image.

5. The method of claim 1 wherein the tissue relaxation parametric maps comprise $T_1$, $T_2$, and $\rho$ maps, and wherein the magnetic/radiofrequency field maps comprise $B_0$ and $B_1$ maps.

* * * * *